United States Patent [19]

Keller

[11] Patent Number: 4,989,758
[45] Date of Patent: Feb. 5, 1991

[54] DOUBLE DELIVERY CARTRIDGE FOR TWO MASSES

[76] Inventor: Wilhelm A. Keller, Riedstrasse 1, CH-6330 Cham, Switzerland

[21] Appl. No.: 427,999

[22] Filed: Oct. 26, 1989

Related U.S. Application Data

[63] Continuation of Ser. No. 92,770, Sep. 3, 1987, abandoned.

[30] Foreign Application Priority Data

Sep. 14, 1986 [CH] Switzerland ............... 03680/86

[51] Int. Cl.$^5$ ............................................... B67D 5/52
[52] U.S. Cl. .................................. 222/137; 222/94; 222/145; 222/327
[58] Field of Search ............... 222/145, 137, 135, 136, 222/488, 489, 484, 548, 555, 94, 541, 129; 206/219; 215/6; 220/20, 22

[56] References Cited

U.S. PATENT DOCUMENTS

| | | | |
|---|---|---|---|
| 2,589,743 | 3/1952 | Snaith | 222/94 |
| 3,323,682 | 6/1967 | Creighton, Jr. et al. | 222/94 |
| 3,390,814 | 7/1968 | Creighton, Jr. et al. | 222/137 |
| 3,570,719 | 3/1971 | Schiff | 222/137 |
| 3,828,980 | 8/1974 | Creighton et al. | 222/137 |
| 4,040,420 | 8/1977 | Speer | 604/82 |
| 4,240,566 | 12/1980 | Bergman | 222/135 |
| 4,260,077 | 4/1981 | Schroeder | 222/137 |
| 4,359,049 | 11/1982 | Redl et al. | 604/227 X |
| 4,366,919 | 1/1983 | Anderson | 222/137 |
| 4,378,069 | 3/1983 | Franco | 222/541 X |
| 4,690,306 | 9/1987 | Stäheli | 222/137 X |
| 4,767,026 | 8/1988 | Keller et al. | 222/137 |
| 4,771,919 | 9/1988 | Ernst | 222/94 X |
| 4,838,920 | 9/1985 | Drake | 222/137 X |

FOREIGN PATENT DOCUMENTS 124852 11/1984 European Pat. Off. .

Primary Examiner—Kevin P. Shaver
Attorney, Agent, or Firm—Darby & Darby

[57] ABSTRACT

Double cartridges for two-component compounds manufactured in one piece by injection molding have separate reservoir cylinders. Discharge channels starting from each cylinder space are separated in a common orifice by two wall sections which start from separate cylinder walls and are brought in duplicate up to the channel end; in addition, the channels receive a separate closure inserted axially from the outside. The one-piece connection at the orifice occurs either by an end-face web between the wall sections or through circumferential sections of an orifice ring embracing the channels. As a result, the diffusion paths in the plastic material of the cartridge are extremely long. Yet the advantages of the one-piece double cartridge with respect to manufacture and handling are preserved. A variant with longitudinally bored closure remaining in the orifice is described, which forms together with a rotatable slide element a seal intended for opening and closing.

13 Claims, 2 Drawing Sheets

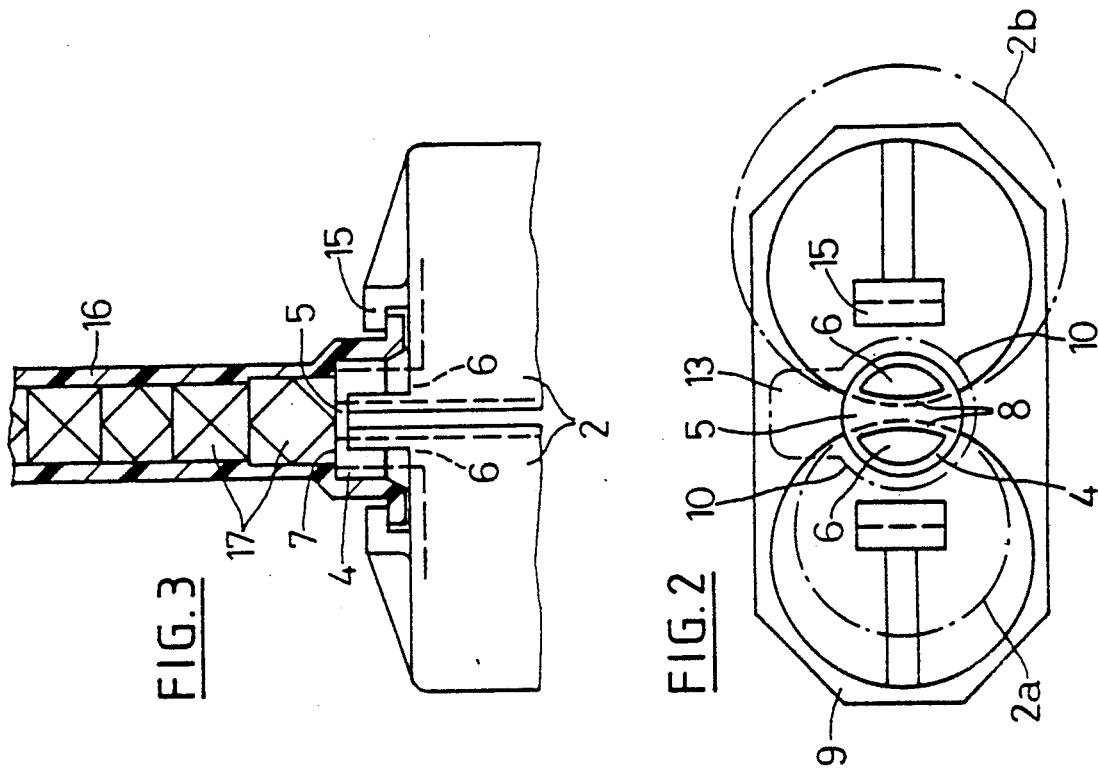
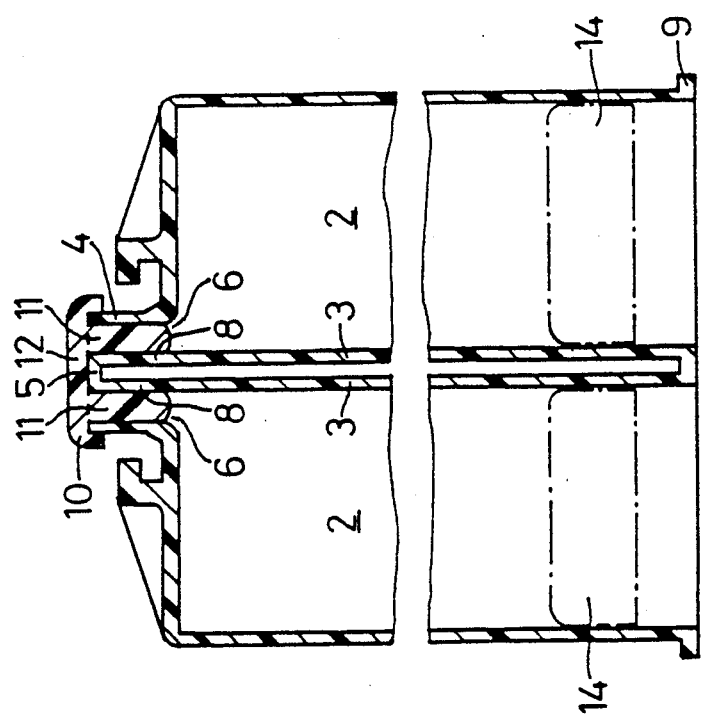

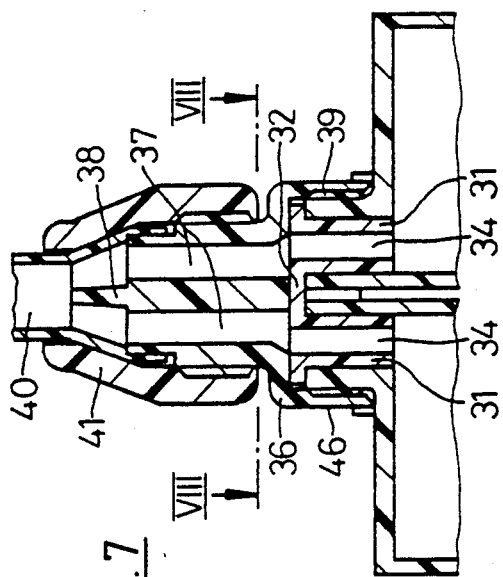
FIG.4
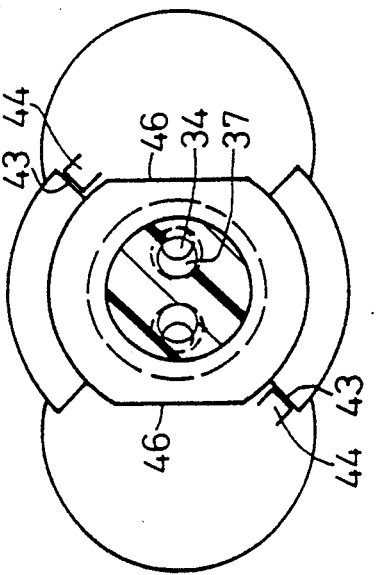
FIG.7
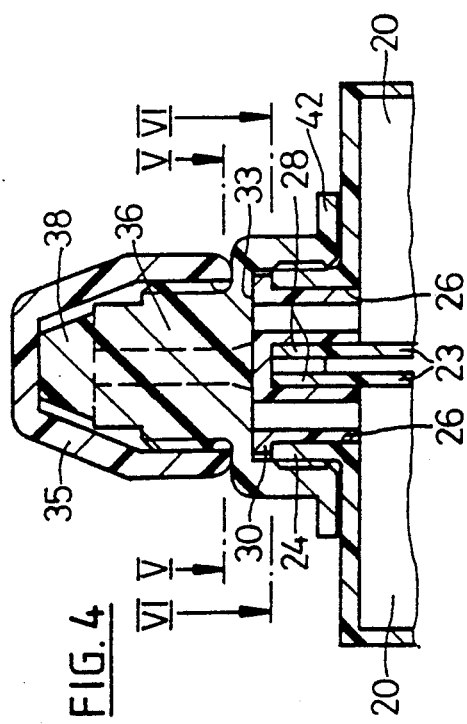
FIG.5
FIG.6
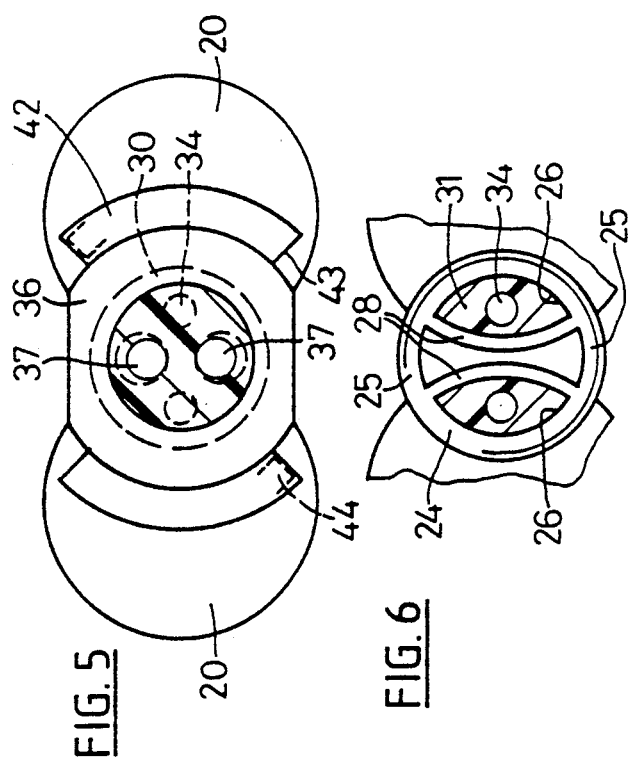
FIG.8

DOUBLE DELIVERY CARTRIDGE FOR TWO MASSES

This is a continuation of application, Ser. No. 092,770, filed Sept. 3, 1987, now abandoned.

FIELD OF THE INVENTION

The invention relates to a double discharge cartridge for two-component compounds, having two reservoir cylinders arranged with parallel axes side by side, and having an orifice on the end face which is common to both cylinders and which connects them in one piece and which contains two axial discharge channels, each starting from a cylinder space.

BACKGROUND OF THE INVENTION

Such double cartridges, normally made of plastic by injection molding, are used for storing and selling two substance components that belong together, which during processing are mixed and react together chemically, the mixture becoming solid or cured. Examples of such two-component compounds are adhesives, grouting compounds, dental impression compounds, etc. The discharge of the two components through the orifice during processing occurs by actuation of a feed piston present in each reservoir cylinder, where, as a rule, a continuous-flow mixer is connected to the cartridge orifice. Because of the high viscosity of the compounds and the flow resistance of the mixer, considerable forces must be exerted on the pistons, and there result correspondingly high pressures in the cylinders.

Since a relatively long time passes between filling of the components into the cartridge and the processing, typically several months to one year, known double cartridges of this kind present the problem that constituent parts of one or of both components will diffuse through the thin plastic walls and the reaction will start prematurely, i.e., already during storage. The curing or at any rate the thickening or "nodulation" connected therewith is troublesome especially in the common orifice region, because this often makes the discharge and processing impossible and hence the entire content of the cartridge becomes worthless. Naturally, the two components can be filled, as is also known, into separate discrete cartridges or cylinders (hence not connected in one piece), which are joined together only during processing at the mixer. With such multi-part production, however, greatly increased mold and assembly costs arise. The handling (filling, selling, storage, use) of the discrete cartridges becomes complicated and, lastly, also mix-ups in processing cannot be ruled out, in that inadvertently components not belonging together or two identical (non-reacting) components, are brought together.

OBJECTS AND SUMMARY OF THE PRESENT INVENTION

It is an object of the invention, therefore, for double discharge cartridges to be made in one piece of plastic, while maintaining their advantages in production, handling and use, in order to prevent a premature reaction of the components in the cartridge or to make possible a considerably prolonged shelf life.

The solution of this task consists, according to the invention, in that the two discharge channels are separated by two wall sections starting from separate cylinder walls and are brought in duplicate up to the channel end and that they receive a separate closure inserted axially from the outside.

Due to the fact that in this design the "creep paths" in the plastic material are greatly lengthened — on the one hand by the double-wall separation of the discharge channels and on the other hand by the inserted closure — the harmful diffusion between the stored components is suppressed virtually completely. Another advantage results from the fact that the axial channels, which are necessarily open for the insertion of the closure, allow in injection molding the satisfactory supporting and centering of the cylinder mold cores, and this, in turn, ensures uniform cylinder wall thicknesses.

Several variations of the invention are envisioned. Certain variations relate to different designs of the orifice, and one variation relates to the closure. According to one form of the invention, the closure variation forms, for the duration of the storage of the filled cartridge, a seal which, however, must be removed before discharge, i.e., before the processing of the cartridge content. In one design according to the invention, on the contrary, the closure remains in the cartridge orifice and is a constituent part of a slide seal, which can be opened for discharge and, if desired, closed again; certain variations of the invention relate to the appropriate design of such a seal or of an associated slide element.

In the following, several embodiment examples of the double discharge cartridge of the invention are described in connection with the drawing.

BRIEF DESCRIPTION OF THE DRAWINGS

In the drawing:

FIG. 1 shows a first form of realization in longitudinal section;

FIG. 2 is the end view of the double cartridge according to FIG. 1, the closure being indicated in dash-dot lines;

FIG. 3 shows the same double cartridge in side view (cylinder partially broken away, after removal of the closure and with connected continuous-flow mixer drawn in section;

FIG. 4 shows the head portion of an additional form of realization with rotatable, closed slide seal in longitudinal section;

FIG. 5 is a section along line V—V in FIG. 4;

FIG. 6 is a section along line VI—VI in FIG. 4 (slide element omitted);

FIG. 7 is a section analogous to FIG. 4, but with the seal opened and with connected continuous-flow mixer; and FIG. 8 is a section along line VIII—VIII in FIG. 7.

DESCRIPTION OF THE PREFERRED EMBODIMENTS

The double-discharge cartridge according to FIGS. 1 to 3 comprises two reservoir cylinders 2 with the cylinder walls 3 which, together with a common orifice 4, are made in one piece as an injection molding of plastic. The two cylinders 2 each contain a feed piston 14 (indicated in dash-dot lines) and may be connected at the rear end by a flange 9. Starting from each of the cylinders 2 arranged with parallel axes side by side is a discharge channel 6 extending axially through the orifice 4. Inside the orifice 4, the discharge channels 6 are completely separated with double walls by two wall sections 8 which start from the separate cylinder walls 3; preferably at least the inner side of the wall sections 8 is cylindrical and continuously extends the inner surface of each cylinder 2, as can be seen from FIG. 2. Only at the front end of the discharge channels 6 the wall sections 8 are connected by a flat web 5 which (together with the end-face edge of the orifice 4) defines an end-face plane 7 of the orifice.

A separate closure 10, axially inserted into the orifice 4 from the outside and preferably made of plasticized plastic or rubber, comprises two projections 11, each adapted to the cross-section of a discharge channel 6. The two projections 11 are connected by a flange 12, the edge of which extends over the end-face edge of the orifice 4. Flange 12 is provided, in addition, with a grip 13 (FIG. 2), to facilitate removal of the closure 10 from the orifice.

With the double cartridge according to FIG. 1 with inserted closure 10, storage of filled components is possible for a long time, without the occurrence of an undesired premature reaction due to diffusion through the plastic material of the cartridge. Since the channels 6 are separated with double walls also in the orifice and there is a physical connection exclusively on the end face via the web 5 while, in addition, the closure 10 with the projections 11 keeps the filled components away from the channels 6, there exists an extremely long "creep path" in the plastic material between the two cylinder spaces, virtually preventing diffusion. Yet the double cartridge including the orifice is made as a one-piece plastic injection molding. The axial discharge channels, open in front, make it possible to center the cores for the cylinder spaces in the injection mold satisfactorily. Owing to this, constant wall thicknesses can be maintained for the cylinder walls 3, whereby the required strength and form stability under occurring internal pressures is achieved even with relatively thin walls.

With only slight adaptations at the orifice, double cartridges with different cylinders 2a and 2b (indicated in FIG. 2 in dash-dot lines) can also be manufactured in the same manner for two-component systems, the components of which are not to be mixed in equal parts.

The double cartridge according to FIGS. 1 to 3 has on the end face, in a manner known in itself, a bayonet socket 15 for the attachment of a continuous-flow mixer 16 (FIG. 3), and the orifice is designed for tightly attaching such a mixer. When taking the cartridge into operation for discharging and processing the two-component compound, first the closure 10 must be removed from the orifice, whereupon the mixer 16 is connected. In so doing, on the one hand, an inner shoulder of the mixer tube is pressed against the end-face edge and, on the other hand, the first of the schematically shown mixing elements 17 is pressed with its inlet edge against web 5 of the orifice.

The two cylinders 20 of the double cartridge made in one piece according to FIGS. 4 to 8 also have separate cylinder walls 23 and, starting from each cylinder space, discharge channels extending axially through the common orifice 24. The channels 26, open on the end face, are in turn separated by double walls up to the end of the channels by wall sections 28 which start from the cylinder walls 23. In contrast to the preceding embodiment, here an end-face connecting web between the wall sections 28 is missing, but in the region of the orifice 24 a one-piece connection between the two cylinders 20 is established by sections 25 of a closed ring which is integrally formed or molded on at the end faces of both reservoir cylinders and embraces both discharge channels 26.

Here, too, the closure 30 inserted axially from the outside has two projections 31 adapted to the cross-section of the discharge channels 26, which projections are connected by a flange 32 over the end face of the orifice. In this example, however, each projection 31 contains a longitudinal bore 34, which traverses also the flange 32. The outer face 33 of the flange is formed as a seal surface and intended for cooperation with a slide element 36 rotatably guided at the orifice 24 by means of a fine thread 39. Here, therefore, the closure 30 for substance discharge is not to be removed from the orifice but remains as a constituent part of a slide seal described below, which can be opened and closed.

The essential advantages with respect to one-piece manufacture of the double cartridge and, in particular, inhibition of diffusion exist also in this variant. The material components filled into the cylinders do indeed normally fill the longitudinal bores 34 in the closure up to the seal surface 33. But because of the physical separation from the projections 31 to the ring 24 or the wall sections 28, diffusion of the content is made difficult (FIG. 6) and is possible inside the ring only via the sections 25. As a variant it would be possible also first to close the cylinder-side entrance of the bores 34 by a thin film or foil (not shown) integrally formed at the closure and thus to keep the cartridge contents away from the bores 34 during storage; as discharge begins, these seal films are caused to burst by the internal pressure in the cylinder and the bores are thereby freed.

The slide element 36 also has two longitudinal bores 37, which connect to the seal surface 33 of the closure. The cap of the slide element 36, spanning the orifice and the closure 30, has lateral key/wrench faces 46 and a flange 42, from which two opposite sectors of 90° each are cut out.

FIGS. 4 and 5 show the seal in the closed position, in which the longitudinal bores 37 of the rotatable slide element 36 are offset relative to the longitudinal bores 34 of closure 30 (FIG. 5). The filled double cartridges come on the market and are stored until used in this closed position; the front portion of the slide element may be protected by means of a cap 35. The fine thread 39 between orifice 24 and slide element 36 is appropriately formed to be stiff, and the slide element is not yet completely tightened up to the stop, although far enough to exert on the seal surface 33 a pressure sufficient to seal the bores 34.

For the purpose of discharging and processing the cartridge content, the slide element 36 is rotated onward 90° into the open position per FIGS. 7 and 8. In so doing, flange 32 is compressed additionally to correspond to one fourth the pitch, this being desirable in view of the high internal pressure occurring during discharge. For exact fixing of the opening position, in which the bores 37 are to communicate with the bores 34, expediently rotary stops for the slide element 36 are provided. In the present case, such stops are formed by radial abutment edges 43 at flange 42 and by cams 44 projecting from the cylinders 20 on the end face. Unless the entire cartridge contents are processed all at once, the seal can be opened and closed several times; optionally, corresponding rotary stops (not shown) can be provided also for the closed position.

The slide element 36 is formed at its front portion for connecting a continuous-flow mixer 40. The latter is placed on after removal of the protective cap 35 and is tightened by means of a cap nut 41 at the slide element 36. A partition 38 of the slide element projecting over the end of the bores 37 in axial direction provides for separate feed of the two components up to transfer to the mixing elements of the mixer 40 (not shown).

In the design of the orifice and of the closure (with or without rotary seal), a number of variants are, of course, possible. Thus, it may be desirable in the realization according to FIGS. 1 to 3 to reinforce the orifice by integrally formed ring sections forming a closed cylindrical orifice ring, corresponding to the sections 25 per FIG. 6. Besides, the use of a closure to be removed before discharge or of a longitudinally pierced closure in conjunction with a slide element does not depend on the respective configuration of the orifice. Likewise, a rotatable connection between orifice and slide element may be realized by means other than by screw thread.

Lastly, it is also readily conceivable to apply the measures of the invention for inhibiting diffusion and characteristics of the seal analogously to triple discharge or multiple discharge cartridges (for three or more components), should such systems be introduced in the future.

While the foregoing description and drawings represent the preferred embodiments of the present invention, it will be obvious to those skilled in the art that various changes and modifications may be made therein without departing from the true spirit and scope of the present invention.

What is claimed is:

1. A double discharge cartridge molded in one piece for two-component compounds, said cartridge comprising two reservoir cylinders arranged with parallel axes die by side, said cartridges having an orifice with an end face which is common to both cylinders and which connects them in one piece, said orifice containing two axial discharge channels, each discharge channel starting from a respective cylinder, the two discharge channels being separated by two wall sections, said wall sections extending continuously from separated cylinder walls, said extending wall sections being separated up to the end face, forming a diffusion barrier between said channels.

2. A double discharge cartridge molded in one piece for two-component compounds, said cartridge comprising two reservoir cylinders arranged with parallel axes side by side, said cartridge having an orifice with an end face which is common to both cylinders and which connects them in one piece, said orifice contains two axial discharge channels, each discharge channel starting from a respective cylinder space, the two discharge channels being separated by two wall sections, said wall sections extending continuously from separated cylinder walls, said extending walls being separated up to the end face forming a diffusion barrier between said channels, said discharge channels being adapted to receive a closure inserted axially from outside the cartridge, closure having two projections each adapted to the respective crosssection of one said discharge channel and connected by a flange; said closure when inserted forming a seal to be removed prior to discharging the two-component compounds from the discharge channels; said projections extending into said discharge channels substantially past the end face to prevent diffusion of the component compounds particularly during long-term storage.

3. Double discharge cartridge molded in one piece for two-component compounds, said cartridge comprising two reservoir cylinders arranged with parallel axes side by side, and having an orifice on an end face which is common to both cylinders and which connects them in one piece and which contains two axial discharge channels, each starting from a cylinder space, the two discharge channels being separated by two wall sections extending continuously from separate cylinder walls in duplicate up to the channel ends so that a free space forming a diffusion barrier is provided therebetween, wherein said discharge channels are adapted to receive a separate closure inserted axially from outside the cartridge, said cartridge also including a closure which comprises two projections each adapted to the cross-section of a discharge channel and connected by a flange, and, wherein each projection has a longitudinal bore traversing the flange and the outer surface of the flange forms a seal surface extended to cooperate with a slide element rotatably guided at the orifice.

4. Double discharge cartridge according to claim 2 or claim 3, wherein the two wall sections are connected at the channel end by a flat web defining said end-face plane of the orifice.

5. Double discharge cartridge according to claim 2 or claim 3, wherein the two wall sections are connected by sections of a ring which is integrally formed at end-face sides of both reservoir cylinders and embraces both discharge channels.

6. Double discharge cartridge according to claim 2 or claim 3, wherein inner sides of the wall sections are curved.

7. Double discharge cartridge according to claim 2, wherein the orifice is designed for connection of a continuous-flow mixer.

8. Double discharge cartridge according to claim 3, wherein the slide element contains two longitudinal bores and in rotatable selectively into an opening position or a closing position, in which said longitudinal bores either communicate with those of the closure or are offset relative to them.

9. Double discharge cartridge according to claim 8, wherein the orifice and slide element are connected by a fine thread and pressurize the flange of the closure with different axial pressures in the closing and opening positions.

10. Double discharge cartridge according to claim 8, wherein rotary stops for the slide element are provided which fix at least the opening position thereof.

11. Double discharge cartridge according to claim 3, wherein the slide element is provided with a key face.

12. Double discharge cartridge according to claim 3, wherein the sliding element is formed as a connection of a continuous-flow mixer.

13. Double discharge cartridge according to claim 3, wherein the longitudinal bores of the projections are closed on the entrance side by a seal destroyable by internal pressure in the cylinder.

* * * * *

UNITED STATES PATENT AND TRADEMARK OFFICE
CERTIFICATE OF CORRECTION

PATENT NO. : 4,989,758

DATED : February 5, 1991

INVENTOR(S) : WILHELM A. KELLER

It is certified that error appears in the above-identified patent and that said Letters Patent is hereby corrected as shown below:

On the cover page at [76], the Inventor is:

-- Wilhelm A. Keller
       Grundstrasse 12
       CH-6343 Rotkreuz
       Switzerland --

Signed and Sealed this

Eighteenth Day of August, 1992

*Attest:*

DOUGLAS B. COMER

*Attesting Officer*      *Acting Commissioner of Patents and Trademarks*